(12) United States Patent
MacLaughlin

(10) Patent No.: US 8,515,510 B2
(45) Date of Patent: Aug. 20, 2013

(54) ELECTROADHESIVE MEDICAL DEVICES

(75) Inventor: Scott MacLaughlin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1177 days.

(21) Appl. No.: 12/414,985

(22) Filed: Mar. 31, 2009

(65) Prior Publication Data

US 2010/0249553 A1     Sep. 30, 2010

(51) Int. Cl.
*A61B 5/1455*     (2006.01)

(52) U.S. Cl.
USPC ............................ 600/323; 600/324; 600/344

(58) Field of Classification Search
USPC ................................................ 600/309–344
See application file for complete search history.

(56) References Cited

U.S. PATENT DOCUMENTS

| | | | |
|---|---|---|---|
| 2,025,123 A | | 12/1935 | Rahbek |
| 2,568,824 A | | 9/1951 | Rahbek |
| 4,491,623 A | | 1/1985 | Kokubo et al. |
| 5,090,410 A | * | 2/1992 | Saper et al. ..................... 602/41 |
| 5,106,675 A | | 4/1992 | Masayasu et al. |
| 5,746,201 A | | 5/1998 | Kidd |
| 5,839,306 A | | 11/1998 | Nunuparov |
| 6,124,964 A | | 9/2000 | Imanishi et al. |
| 6,382,305 B1 | | 5/2002 | Sano |
| 6,390,302 B1 | | 5/2002 | Vagiz et al. |
| 6,789,679 B2 | | 9/2004 | Vagiz et al. |
| 6,791,817 B2 | | 9/2004 | Allison et al. |
| 6,816,266 B2 | | 11/2004 | Varshneya et al. |
| 6,967,652 B1 | | 11/2005 | Nubling et al. |
| 7,112,175 B2 | | 9/2006 | Gopinathan et al. |
| 7,161,484 B2 | | 1/2007 | Tsoukalis |
| 7,257,438 B2 | | 8/2007 | Kinast |
| 7,297,119 B2 | | 11/2007 | Westbrook et al. |
| 7,305,262 B2 | | 12/2007 | Brodnick et al. |
| 7,435,222 B2 | | 10/2008 | Gopinathan et al. |
| 7,551,419 B2 | | 6/2009 | Pelrine et al. |
| 2002/0082668 A1 | * | 6/2002 | Ingman ........................... 607/98 |
| 2005/0017864 A1 | | 1/2005 | Tsoukalis |
| 2005/0021028 A1 | | 1/2005 | Palanker et al. |
| 2007/0123756 A1 | | 5/2007 | Kitajima et al. |
| 2007/0129622 A1 | | 6/2007 | Bourget et al. |
| 2007/0142715 A1 | | 6/2007 | Banet et al. |
| 2008/0089002 A1 | | 4/2008 | Pelrine et al. |

(Continued)

FOREIGN PATENT DOCUMENTS

| DE | 10211395 | 10/2003 |
|---|---|---|
| EP | 1986543 | 11/2008 |

(Continued)

OTHER PUBLICATIONS

International Search Report and Written Opinion for PCT/US2010/026962 dated Apr. 19, 2011, 15 pgs.

(Continued)

*Primary Examiner* — Eric Winakur
*Assistant Examiner* — Marjan Fardanesh
(74) *Attorney, Agent, or Firm* — Fletcher Yoder

(57) ABSTRACT

A method and system for attaching medical devices to a patient are provided. In accordance with an embodiment, a medical device is formed with or is coupled to an attachment structure including a plurality of electrodes capable of generating differential voltages at adjacent electrodes, to thereby provide electrostatic adhesion with the tissue of a patient. In an embodiment, the attachment structure includes an insulative material between the respective electrodes of the plurality of electrodes.

17 Claims, 7 Drawing Sheets

(56) References Cited

U.S. PATENT DOCUMENTS

| | | |
|---|---|---|
| 2008/0091089 A1 | 4/2008 | Guillory et al. |
| 2008/0091090 A1 | 4/2008 | Guillory et al. |
| 2008/0119842 A1 | 5/2008 | Palanker et al. |
| 2008/0211341 A1 | 9/2008 | Pelrine et al. |
| 2011/0251473 A1* | 10/2011 | Moran et al. .................. 600/373 |

FOREIGN PATENT DOCUMENTS

| | | |
|---|---|---|
| SU | 1291395 | 2/1987 |
| WO | 9420984 | 9/1994 |
| WO | 02/32121 A2 | 5/2001 |
| WO | 0241084 | 5/2002 |
| WO | 2005053530 | 6/2005 |

OTHER PUBLICATIONS

SRI International's Electroadhesive Robots: "Electroadhesive Robots; Enabling wall-climbing robots for security/military, inspection, and service applications"; www.sri.com/rd/electroadhesions.html, Dec. 1, 2008.

* cited by examiner

ELECTROADHESIVE MEDICAL DEVICES

BACKGROUND

The present disclosure relates generally to medical devices and, more particularly, to external medical devices that may be attached to a patient's tissue using electroadhesion.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of monitoring devices have been developed for monitoring many such physiological characteristics. These monitoring devices often provide doctors and other healthcare personnel with information that facilitates provision of the best possible healthcare for their patients. As a result, such monitoring devices have become a fixture of modern medicine.

Often the monitoring devices, or probes or sensors associated with the monitoring devices, are applied to the patient, such as to the skin or mucosal tissue of the patient. For example, pulse oximetry sensors may be applied to a finger, forehead, or ear lobe of a patient. Similarly, electrodes for use with an electrocardiograph (ECG) or electroencephalograph (EEG) device may be respectively applied to the torso and the head of a patient. In addition to monitoring devices, some treatment or therapy devices may also be attached to the patient, such as a mask for use with ventilating a patient.

In some instances such applied devices may be attached using adhesive compositions. However such adhesive compositions may make removal of the device uncomfortable and may leave a tacky residue at the site of application. Further, use of adhesive compositions may be unsuitable for certain patients, such as burn victims, the elderly, or neonates, whose skin may be sensitive or damaged.

Likewise, the use of mechanical attachment mechanisms, such as straps, bands, and wraps, may also be unsatisfactory. In particular, such mechanical attachments may prevent or limit patient movement. Further, mechanical attachment mechanisms may be subject to over- or under-tightening when applied, which may result in suboptimal performance of the medical device and/or patient discomfort.

BRIEF DESCRIPTION OF THE DRAWINGS

Advantages of the invention may become apparent upon reading the following detailed description and upon reference to the drawings in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed herein, electroadhesion may be understood to refer to the adhesion or attachment of two objects by means of electrostatic forces acting between the objects. One aspect of electroadhesion is that it may allow an object to be adhered to another object regardless of whether the other object is made of conductive or non-conductive materials or whether the other object is clean, dirt, wet, or otherwise unsuitable for other forms of attachment, such as by means of chemical adhesives.

As discussed herein, electroadhesion may be used to attach a medical device (such as a probe, sensor, or electrode of a monitoring system or an applicator or application, e.g., a mask, bandage, wrap, and so forth, associated with a treatment or therapy) to a patient. The electroadhesive forces may be generated using electrodes placed within or on the medical device which generate electrostatic forces to couple the medical device to the patient. This electroadhesive force may be powered by a source external or internal to the medical device and may be turned on or off or otherwise adjusted by controlling the voltage applied to the electrodes within the medical device. In this manner, the medical device may be attached to and detached from a patient simply by turning the generation of the electroadhesive force on and off, without regard to the condition of the tissue at the attachment site and without patient discomfort. Further, in an embodiment in which the substrate housing the electrodes is deformable the portion of the medical device that interfaces with the patient tissue may conform to the tissue to which the medical device is attached.

Figure 1:
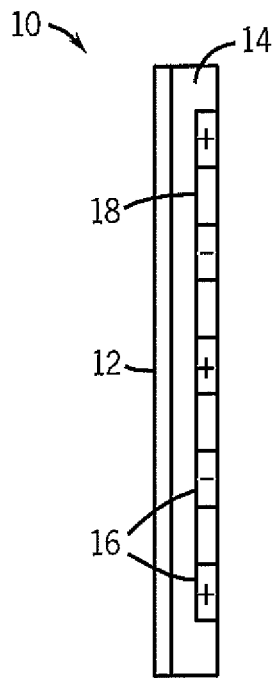
FIG. 1 depicts an attachment substrate in accordance with an embodiment.

By way of further explanation and turning now to FIG. 1, a structure 10 for interfacing with the tissue of a patient is provided. The structure 10 may be attached to or formed integrally with a patient contacting surface of a medical device, such as a patient contacting surface of a sensor, probe) electrode, mask, bandage, and so forth. In an embodiment, the structure 10 may include a backing layer 12 which may secure the remainder of the structure 10 to the medical or other device.

The structure 10 may also include an insulating material 14 which separates electrodes 16. The electrodes 16 may be formed from a suitable conductive composition, such as a metal or alloy (e.g., copper, aluminum, gold, or brass) or a conductive polymer (such as carbon impregnated polymers). Examples of suitable materials for forming the insulating material 14 include, but are not limited to, rubber or elastomeric compositions (including acrylic elastomers, mylar, polyimide, silicones, silicone rubber, payralin, PMDS elastomer, polyurethane, polypropylene, acrylics, nitrite, PVC films, and latex) fiberglass, glass, and ceramic. A conductive trace 18, such as a common electrode or wire, may also be provided in the structure 10 to allow a voltage to be applied to each electrode 16.

Figure 2:
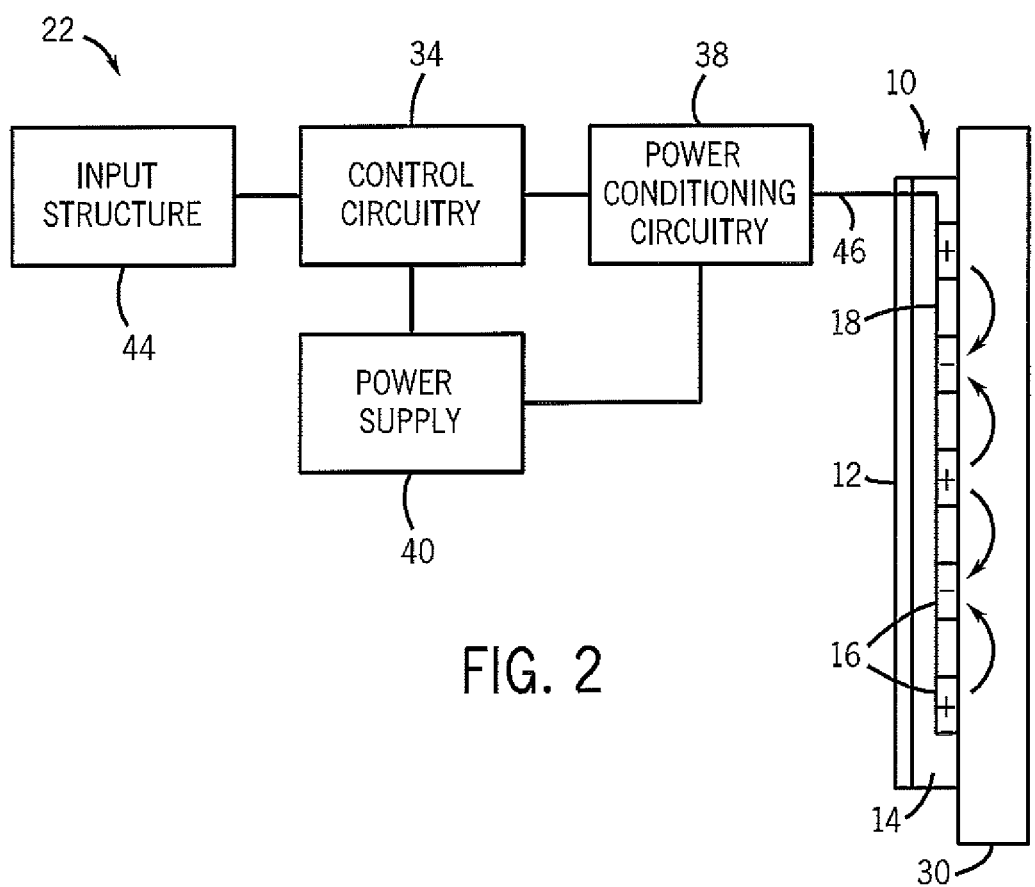
FIG. 2 is a block diagram of an attachment substrate and associated circuitry in accordance with an embodiment.

Referring now to FIG. 2, in operation, operating circuitry 22 may be used to generate an electroadhesive force via the electrodes 16. The operating circuitry 22 may be provided as part of the patient-contacting device, such as part of a sensor, probe, or mask, or as pall of a system electrically connected to the device, such as a monitor, computer, or ventilator. In an embodiment, alternating positive and negative charges are generated at the electrodes 16 and, as a result of the voltage difference between adjacent electrodes 16, an electric field is formed in the substrate 30 (such as, in an embodiment, skin, mucosal tissue, or other tissue) to which the structure 10 is to adhere. The electric field may induce complementary charges in the substrate 30 with respect to the respective electrodes 16, thereby causing electrostatic adhesion between the substrate 30 and the electrodes 16 of the structure 10. Thus, the electrostatic adhesive force generated by the electrodes 16 may act to hold the structure 10 in place relative to the substrate 30. Conversely, the electrostatic adhesive force may be stopped simply by no longer applying the voltage to the electrodes 16, thereby allowing the structure 10 to move freely relative to the substrate 30.

A variety of factors may affect the voltage needed to generate sufficient electroadhesion to attach the structure 10 to the substrate 30. For example, the placement (e.g., spacing, depth) of the electrodes 16, the conductivity of the electrodes 16, the size and/or weight of the structure 10 and any associated device (e.g., a medical device), the composition and/or electrical properties of the insulating material 14, the composition and/or electrical properties of the substrate 30, the extent to which the structure 10 can conform to the shape of the substrate 30, and so forth. Some or all of these factors may determine the size or nature of the power supply 40 used to apply voltages to the electrodes 16 of the structure 10. In an embodiment, a power supply 40 capable of supplying 20 µW/N for the weight held may be sufficient to provide electroadhesion of the structure 10 to the substrate 30 and may provide a clamping pressure of between 0.5 to 1.5 N/cm$^2$ (0.8 to 2.3 lbs/in$^2$).

In an embodiment, the differential voltage between adjacent electrodes 16 of the structure 10 may be between about 500 V to about 10 kV, and may be between about 2 kV and about 5 kV. Further, in an embodiment the positive and negative charges applied to the electrodes 16 may be alternated, i.e., an electrode 16 may be alternated between having a positive and a negative charge while adjacent electrodes 16 may be alternated in a complementary fashion so as to have the opposite charge at any given time. While the electrodes 16 may be alternated between only two voltages (such as between −5 kV and 5 kV), in an embodiment the electrodes 16 may be cycled through more than two voltages, with adjacent electrodes 16 generally having different applied voltages. For example, in an embodiment the electrodes 16 may be alternated through a sequence of three or more voltages, such as −5 kV, 0 V, and 5 kV to generate a suitable electric field in the substrate 30.

Referring once again to FIG. 2, in an embodiment the operating circuitry 22 may include control circuitry 34, power conditioning circuitry 38, and a power supply 40 (such as a battery, AC power from a wall socket, or DC power from a power supply of a medical monitor or device). As used herein, it should be understood that circuitry may include hardware components, software routines, or some combination of hardware and software components. For example, circuitry may be a hardware construct constructed to perform a particular function or may be a programmed processor executing one or more routines to accomplish a function.

In an embodiment, the control circuitry 34 may include circuitry, such as a programmed processor or application-specific integrated circuit (ASIC), that determines the magnitude and timing of the voltages applied to the electrodes 16, as described above. In an embodiment, the control circuitry 34 may allow the electroadhesive force being generated to be switched on and off quickly, e.g., in less than 50 ms. The control circuitry 34 may accept inputs from one or more input structures 44 that control or affect the operation of the control circuitry 34. For example, the input structures 44 may include a dial, knob, or other structure that may be manipulated by a user to control the desired degree of electroadhesion to be exhibited by the structure 10 in attaching to the substrate 30. In addition, the input structures 44 may include one or more pressure sensors, such as may be situated in the attachment structures 10 and/or the substrate 30, that may act upon the control circuitry 34 to increase, decrease, or maintain the electroadhesive force generated by the electrodes 16 based upon a specified or set pressure to be excited by the structure 10 on the substrate 30.

The power conditioning circuitry 38 may perform various functions such as conversion between AC and DC power when appropriate, voltage smoothing, and recovery of stored electrostatic energy. The power conditioning circuitry 38 may receive power from a power supply 40, such as a low-voltage battery, at a lower voltage than is desired to generate the electrostatic forces used in electroadhesion. In an embodiment, the power conditioning circuitry 38 may include a transformer that allows the power conditioning circuitry 38 to perform a voltage step-up in such a circumstance. For example, the power conditioning circuitry 38 may increase a low voltage supplied by the power supply 40, such as a voltage less than 40 V, to a voltage useful in generating electrostatic adhesion, such as above 1 kV. In an embodiment, the power conditioning circuitry 38 may electrically communicate via a lead 46 with a common electrode or other conductive trace 18 that simultaneously communicates with the electrodes 16.

The voltages supplied by the power conditioning circuitry 38 to the electrodes 16 may be AC actuated or DC actuated. In an embodiment, the polarity of charge on each electrode 16 may be alternated at a high frequency to maintain the desired degree of electroadhesion between the structure 10 and the substrate 30. For example, an AC signal with a frequency above 1 Hz may be applied to alternate polarity of the electrodes 16, though higher or lower frequency signals may also be employed.

While FIGS. 1 and 2 depict the electrodes 16 as being on the same surface of the structure 10 and as being generally flush with the substrate-contacting surface of the structure 10, this need not be the case. For example, in an embodiment, the electrodes 16 may be embedded within the insulating material 14 but still capable, when a voltage is applied, of generating a sufficient electric field in a substrate 30 proximate to the structure 10 to allow electroadhesion of the structure 10 to the substrate 30. Likewise, in an embodiment, the electrodes 16 may be placed on a surface of the structure 10 opposite from substrate 30 or may be alternated on different surfaces of the structure 10 (such as having negatively charged electrodes flush or proximate with the substrate 30 and positively charged electrodes offset and disposed on the opposite surface of the insulating material 14). In such an embodiment the electrodes 16 may still be used to generate an electric field which causes electroadhesion between the structure 10 and the substrate 30.

In an embodiment, one or more of the backing layer 12, the insulating material 14 and/or the electrodes 16 may be deformable (e.g., bendable), thereby allowing the substrate 10 to conform to the shape of a surface to which the substrate 10 is attached. For example, in an embodiment, the insulating material 14 may be a layer or sheet of mylar or may be a polymer (such as an acrylic elastomer) with a modulus less than 10 MPa or, in some implementations, less than 1 MPa. Likewise, in an embodiment, the electrodes 16 may be deformable, such as by being constructed from a conductive metal or polymeric composition of a thickness or construction that allows the electrode 16 to be deformed so as to conform to the shape of the substrate 30. Examples of such deformable electrodes 16 may include aluminized mylar or gold-coated polyimide electrodes.

Similarly, the backing layer 12, if present, may be formed from a deformable plastic, polymer, metal, composite, or other such material that would allow the backing layer 12 to deform such that the structure 10 may conform to the shape of the substrate 30. In one embodiment, the backing layer 12 may be an adhesive layer (e.g., a tape or glue layer) suitable for attaching the structure 10 to a medical or other device such that the device may be secured to the substrate 30 when the structure 10 electroadheres to the substrate 30.

Figure 3:
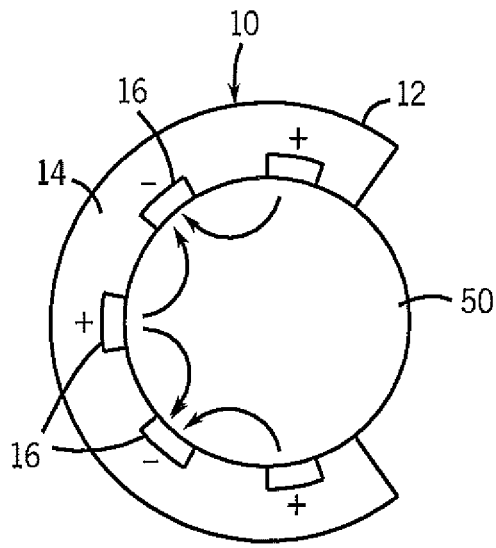
FIG. 3 depicts a deformable attachment substrate applied to a curved surface in accordance with an embodiment.

For example, referring now to FIG. 3, the attachment structure 10 is depicted conforming to a curved surface 50, such as a finger, when applied. While a curved surface 50 is depicted by way of example, other surfaces, including irregular (e.g., non-linear or non-planar) surfaces, may be conformed to by a suitably deformable structure 10. In this manner, the structure 10, and a conformable device mechanically coupled to the structure 10, may conform to and be attached to a substrate 30 (such as the skin, mucosal tissue, or other tissue of a patient) by electroadhesion.

With the foregoing discussion in mind, the following is provided to illustrate one or more medical contexts in which electroadhesion may be employed. For example, in an embodiment, electroadhesion may be used to attach a sensor or probe, such as a spectrophotometric sensor or an ECG or EEG electrode, to a patient's skin or mucosal tissue. By way of example, pulse oximetry may employ a single-use or reusable sensor that is attached to a patient's skin, such as at a finger, ear lobe, or forehead. A block diagram of a system 58 suitable for pulse oximetry or other spectrophotometric applications is provided at FIG. 4 by way of example.

Figure 4:
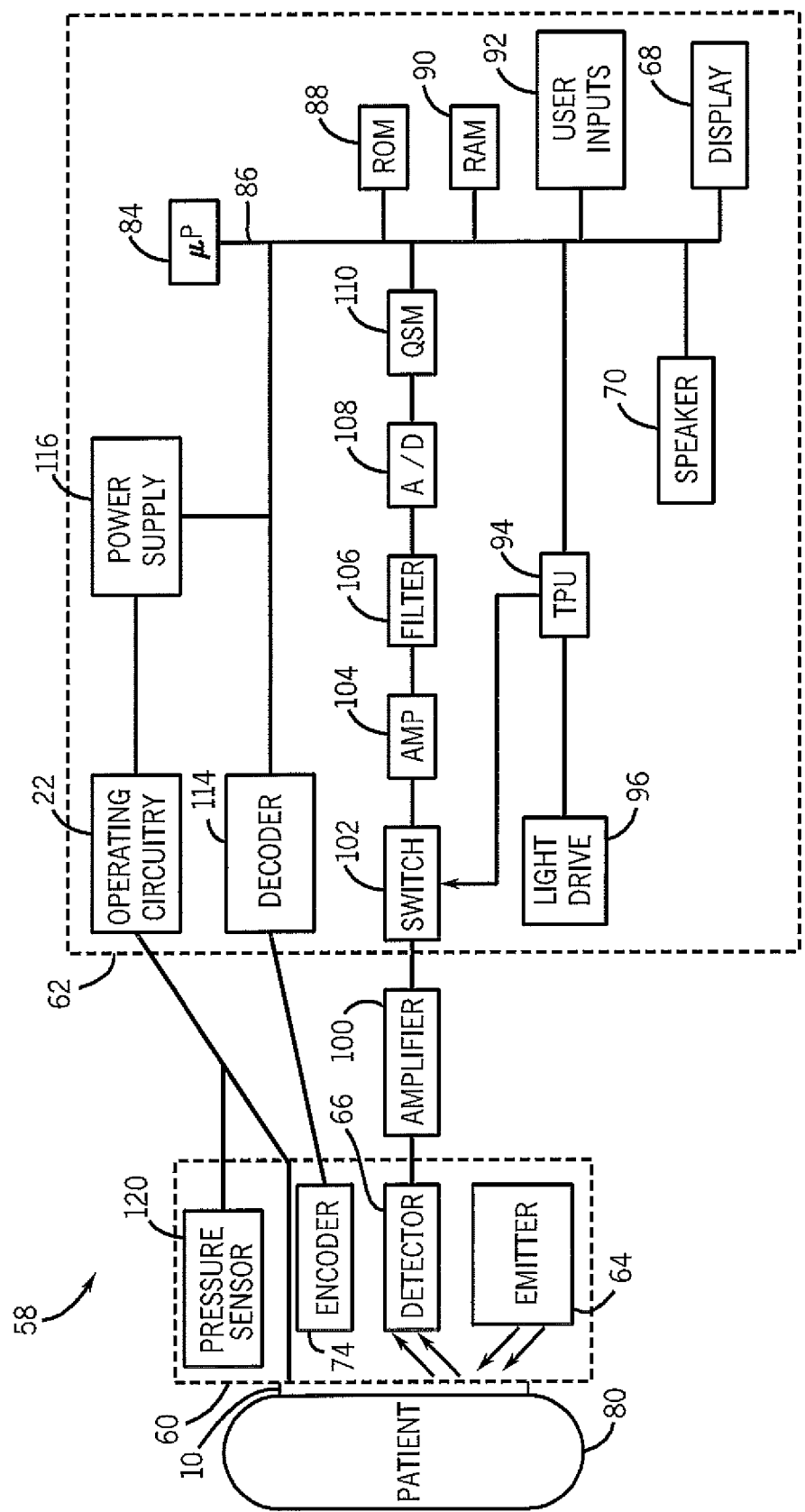
FIG. 4 is a block diagram of a pulse oximeter and sensor coupled to a patient in accordance with an embodiment.

In FIG. 4, the system 58 includes a sensor 60 and a monitor 62, such as a pulse oximeter. The sensor 60 may include an emitter 64 for emitting light at certain wavelengths into a patient's tissue and a detector 66 for detecting the light after it is reflected by and/or transmitted through the patient's tissue. The monitor 62 may be capable of calculating physiological characteristics based on the signals received from the sensor 60 relating to light emission and detection. Further, the monitor 62 may include a display 68 capable of displaying the physiological characteristics, historical trends of the physiological characteristics, other information about the system, and/or alarm indications. The monitor 62 may also include a speaker 70 to provide an audible alarm in the event that the patient's physiological characteristics cross an alarm threshold. The sensor 60 may be communicatively coupled to the monitor 62 via a cable or by a wireless transmission system. In an embodiment, the system 58 may be connected to an additional downstream system or systems, such as a multi-parameter monitor. In addition, the monitor 62 and/or a connected multi-parameter patient monitor may be connected to a network to enable the sharing of information with servers or other workstations.

In an embodiment, the sensor 60 may include the emitter 64, the detector 66, and an encoder 74. It should be noted that the emitter 64 may be capable of emitting at least two or more wavelengths of light and may include one or more light emitting diodes (LEDs) corresponding to the wavelengths emitted. In certain embodiments, one wavelength may be between about 600 nm and about 700 nm and another wavelength may be between about 800 nm and about 1000 nm. Alternative light sources, such as wide- or multi-spectrum light sources, may be used in other embodiments. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the detector 66 may be capable of detecting the intensity of light at the emitted wavelengths. In operation, light enters the detector 66 after passing through the patient's tissue 80. The detector 66 may convert the intensity of the received light into an electrical signal. After converting the received light to an electrical signal, the detector 66 may send the signal to the monitor 62, where physiological characteristics may be calculated based at least in part on the absorption of the emitted wavelengths in the patient's tissue 80.

In an embodiment, an encoder 74 may be provided that contains information about the sensor 60, such as what type of sensor it is (e.g., whether the sensor is intended for placement on a forehead or digit) and the wavelengths of light emitted by the emitter 64. This information may allow the monitor 62 to select appropriate algorithms and/or calibration coefficients for calculating the patient's physiological characteristics. The encoder 74 may, for instance, be a coded resistor which stores values corresponding to the type of the sensor 60 and/or the wavelengths of light emitted by the emitter 64. These coded values may be communicated to the monitor 62, which determines how to calculate the patient's physiological characteristics. In another embodiment, the encoder 74 may be a memory on which one or more of the following information may be stored for communication to the monitor 74: the type of the sensor 60; the wavelengths of light emitted by the emitter 64; and the proper calibration coefficients and/or algorithms to be used for calculating the patient's physiological characteristics. While the depicted embodiment of FIG. 4 illustrates the encoder 74 as being placed in the sensor 60, in other embodiments the encoder 74 may be placed in a cable connecting the sensor 60 to the monitor 62.

Signals from the detector 66 and the encoder 74 may be transmitted to the monitor 62. The monitor 62 generally may include processors 84 connected to an internal bus 86. Also connected to the bus may be a read-only memory (ROM) 88' a random access memory (RAM) 90, user inputs 92, the display 68, and/or the speaker 70. A time processing unit (TPU) 94 may provide timing control signals to a Light drive circuitry 96 which controls when the emitter 64 is illuminated and the multiplexed timing for the different wavelengths. The TPU 94 controls the gating in of signals from detector 66 through an amplifier 100 and a switching circuit 102. These signals may be sampled at the proper time, depending upon which light source is illuminated. The received signal from the detector 66 may be passed through an amplifier 104, a low pass filter 106, and an analog-to-digital converter 108. The digital data may then be stored in a queued serial module (QSM) 110 for later downloading to the RAM 90 as the QSM 110 fills up. In one embodiment, there may be multiple separate parallel paths having the amplifier 104, the filter 106, and the A/D converter 108 for multiple light wavelengths or spectra received.

The processor(s) 84 may determine a physiological characteristic, such as $SpO_2$ and pulse rate or a patient, using various algorithms and/or look-up tables based generally on the value of the received signals corresponding to the light received by the detector 66. Signals corresponding to information about the sensor 60 may be transmitted from the encoder 74 to a decoder 114. The decoder 114 may translate these signals to enable the microprocessor to determine the proper method for calculating the patient's physiological characteristics, for example, based generally on algorithms or took-up tables stored in the ROM 88. In addition, or alternatively, the encoder 74 may contain the algorithms or look-up tables for calculating the patient's physiological characteristics.

While the preceding generally describes the monitoring operations performed by the system 58, as may be appreciated one aspect of a successful monitoring operation is the attachment suitable attachment of the sensor 60 to the surface of the patient 80. To that end, the sensor 60 may include an electroadhesion attachment structure 10, as discussed herein, on part or all of the patient-contacting surface of the sensor 60. In an embodiment, the attachment structure 10 may be provided as strips or patches attached to the surface of the sensor 60. In addition, the attachment structure 10 may be provided as an integral part of the sensor 60, i.e., the electrodes 16, insulating material 14, and conductive trace 18 may all be formed as part of the body of the sensor 60.

In an embodiment, the power supply used to generate the electro-adhesive force may be internal or external to the sensor 60. For example, the power source used to generate the electroadhesive force may be the power source 116 used to power the monitor 62. In such an embodiment voltage may be applied to the electrodes 16 of the structure 10 via a cable connecting the sensor 60 and the monitor 62. The operating circuitry 22 (e.g., the control circuitry 34 and power conditioning circuitry 38 described herein (FIG. 2)) may be located in the monitor 62 as depicted in FIG. 4 or may be located in the sensor 60 or distributed between the monitor 62 and the sensor 60. In addition, the user inputs 92 of the monitor 62 may include a control, e.g., a knob or dial, in communication with control circuitry 34 of the operating circuitry 22 that allow the degree of electroadhesion generated by the structure 10 to be adjusted by a user. In addition, one or more pressure sensors 120 on the sensor 60 may provide a signal indicative of the attachment pressure at the measurement site on the patient 80 to the control circuitry 34 that may allow the degree of electroadhesion generated by the structure 10 to be adjusted to maintain a desired pressure at the site.

Figure 5:
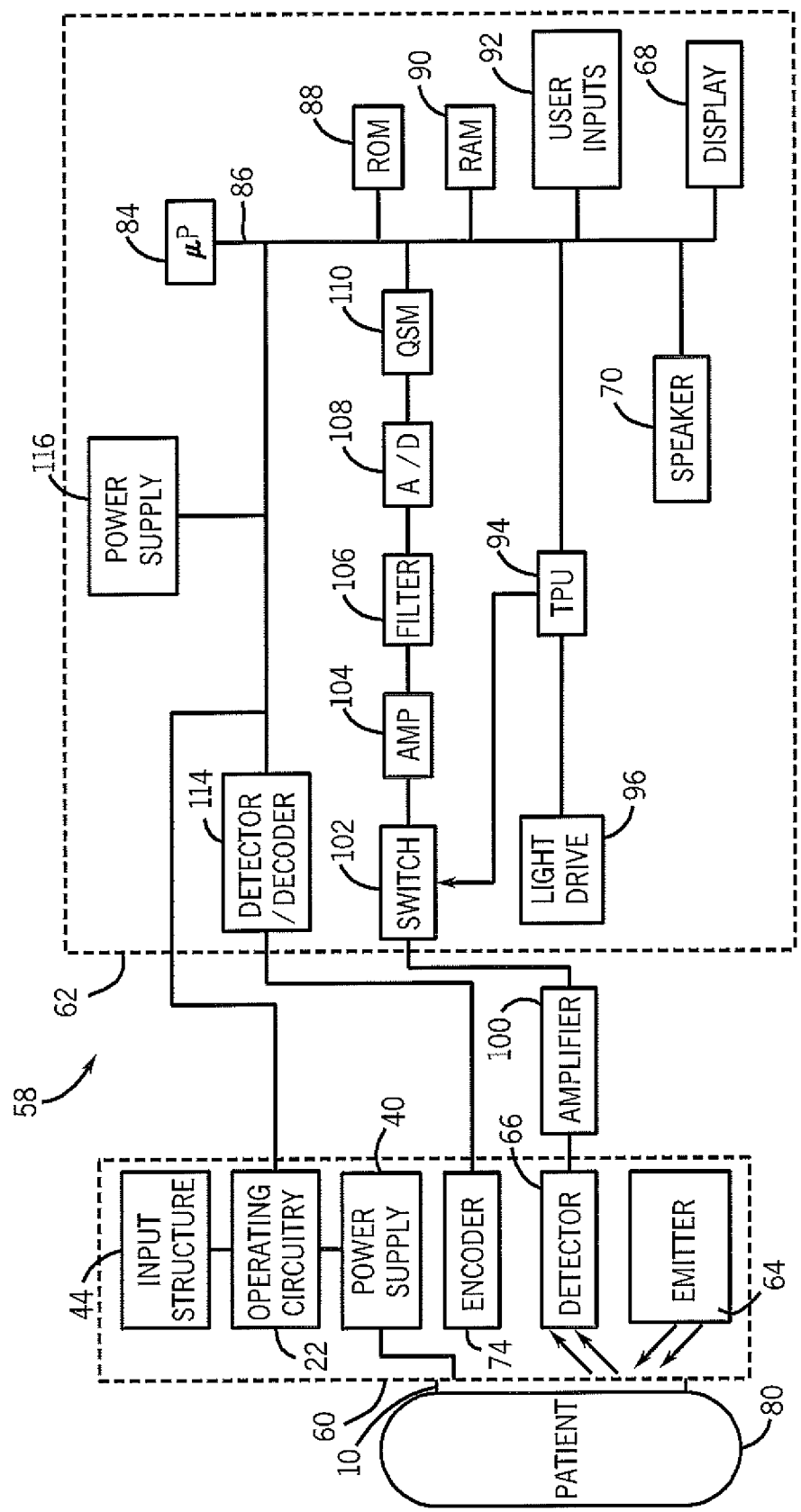
FIG. 5 is a block diagram of a pulse oximeter and sensor coupled to a patient in accordance with an embodiment.

Turning now to FIG. 5, in an embodiment a power supply 40 and operating circuitry 22 are provided on the sensor 60. For example, the power supply 40 may be provided as a battery, such as a low voltage battery, of a size suitable for use in the sensor 60. In an embodiment, the operating circuitry 22 may receive inputs to adjust the degree of electroadhesion generated by the structure 10 from a user input 92 on the monitor 62 (via a cable connecting the monitor 62 and sensor 60), an input structure 44 provided on the sensor 60, or a pressure or other sensor provided on the sensor 60.

Figure 6:
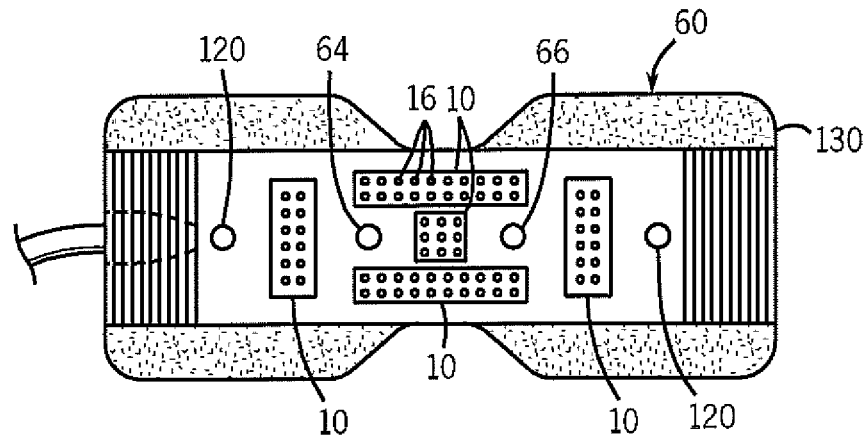
FIG. 6 depicts a bandage-style sensor in accordance with an embodiment.

While the preceding describes the sensor 60 in general terms, the sensor may take a variety of forms, such as a single-use bandage style sensor or a reusable clip-style sensor. Turning to FIG. 6, a bandage-style sensor 130 for use on a finger or forehead is depicted that includes variously shaped attachment structures 10 at different locations on the patient-contacting surface of the sensor. Each structure 10 may include electrodes 16 at which differential voltages are applied, as discussed herein, to generate the desired electrostatic forces with the patient's tissue. Thus, unlike a conventional bandage-style sensor, the bandage-style sensor 130 configured with electroadhesive attachment structures 10 need not be provided with or secured by chemical adhesives or by tape or other materials wrapped about the sensor when applied to a patient's finger, forehead, or other tissue. That is, the electroadhesive forces generated by the structure 10 alone may be sufficient to secure the sensor 130 to the patient.

In an embodiment, the sensor may include one or more pressure sensors 120 that may provide an input to the control circuitry 34 (FIG. 2) controlling the electrostatic fields generated by the electrodes 16. The pressure sensor 120 and/or the control circuitry 34 receiving the input from the pressure sensor 120 may adjust the fields generated by the electrodes 16 to maintain pressure within a specified range, such as above the venous pressure and below the arterial pressure observed at the measurement site. In this manner, a suitable pressure may be applied by the sensor at the measurement site.

Figure 7:
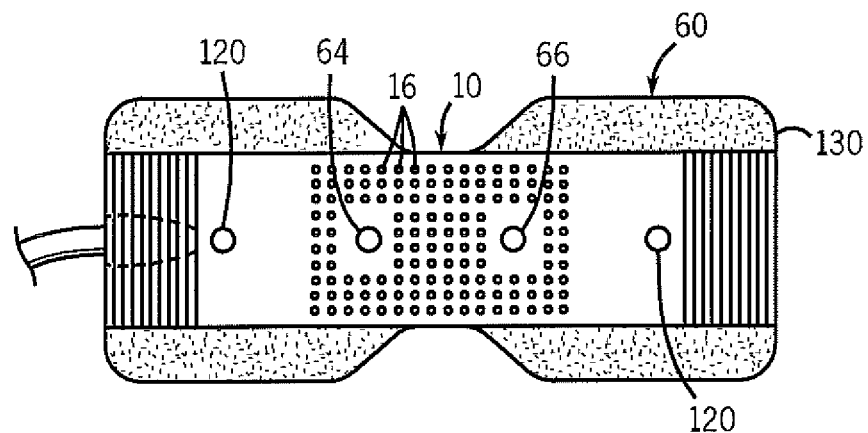
FIG. 7 depicts a bandage-style sensor in accordance with an embodiment.

Turning to FIG. 7, in an embodiment, the body of a bandage-style sensor 130 may itself provide the substrate of the attachment device 10. That is, the insulating material 14, electrodes 16, and other features of the attachment structure 10 may all be formed integrally with the sensor body. As with the previous example, the bandage-style sensor of FIG. 7 may be provided without any additional chemical adhesive on the patient-contacting surface, instead relying on the electroadhesive forces generated by the electrodes 116 to attach the sensor 130 to the patient.

Figure 8:
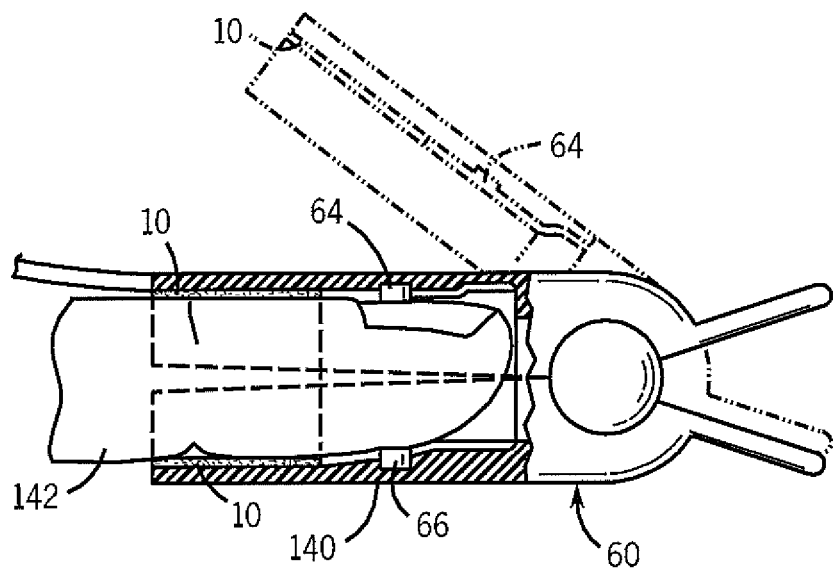
FIG. 8 depicts a clip-style sensor in accordance with an embodiment.

While bandage-style sensors may benefit from electroadhesion, as discussed herein, other sensor types may also benefit. For example, referring to FIG. 8, a reusable clip-style sensor 140 is depicted in open and closed configurations. The clip-style sensor 140 may include one or more attachment structures 10 as described herein, which, when a voltage is applied generate an electroadhesive field to hold the clip-style sensor on the patient, such as the depicted patient's finger 142. As discussed in other contexts, the attachment structures 10 may be attached to part or all of the patient-contacting surfaces of the clip-style sensor 140 or may be constructed integrally with the body or padding of the clip-style sensor 140. In this manner, the clip-style sensor 140 may be held to the patient by electroadhesion, which may or may not be supplemented by a biasing force generated by a spring or other biasing component of the clip-style sensor 140.

Figure 9:
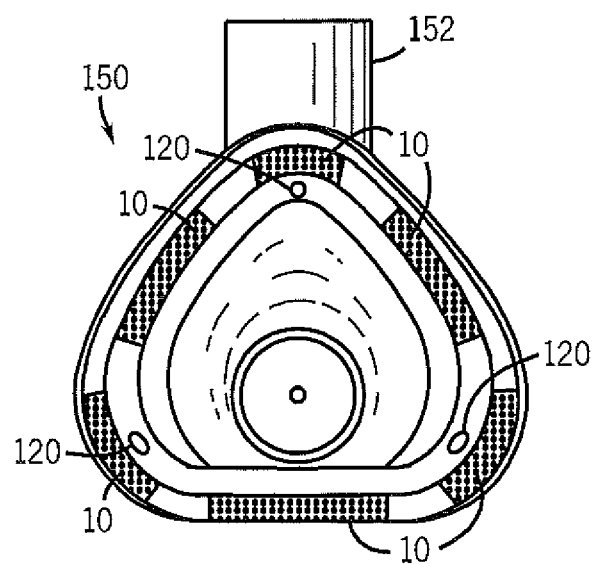
FIG. 9 depicts an end view of a respiratory mask in accordance with an embodiment.
Figure 10:
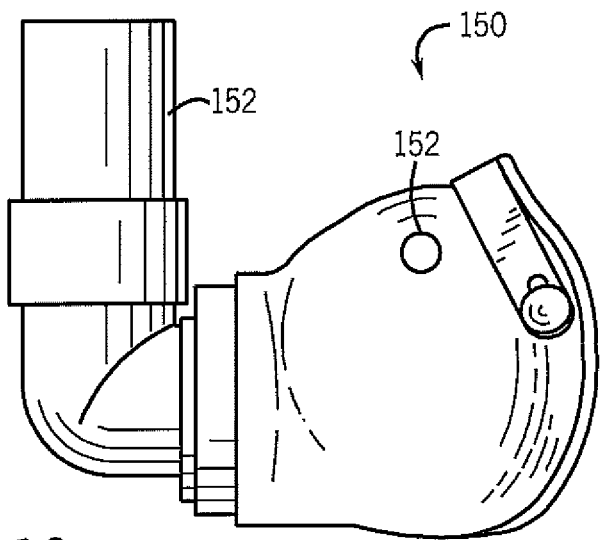
FIG. 10 depicts a side view of a respiratory mask in accordance with an embodiment.
Figure 11:
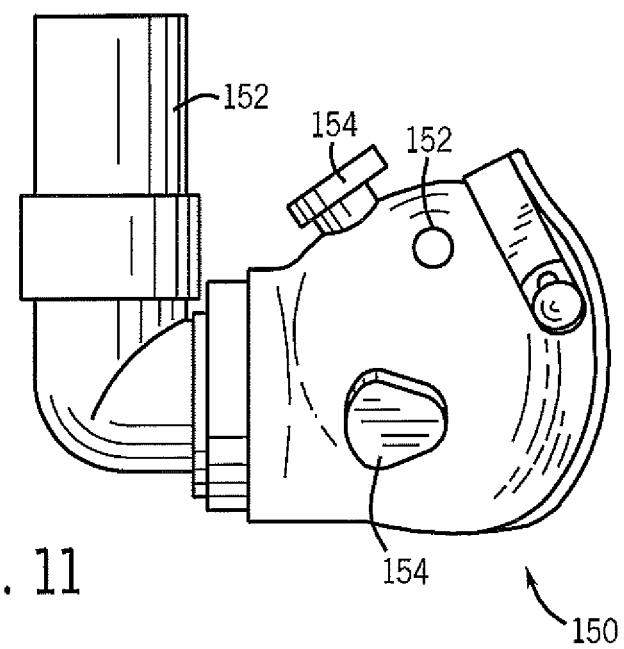
FIG. 11 depicts a side view of a respiratory mask in accordance with an embodiment.

While sensor application, such as for pulse oximetry, is one potential use for electroadhesion, other applications also exist. For example, electroadhesion as discussed herein may be used to attach a therapeutic or treatment device, such as a respiratory mask, to a patient. Turning to FIGS. 9-11, examples of such masks are provided in the form of a continuous positive airway pressure (CPAP) mask 150. Such masks are typically employed as part of a CPAP system that may include a hose connecting the CPAP mask 150 via the connector 152 to a ventilator unit that provides a flow of air to the CPAP mask 150. The CPAP system may also include some form of monitor that regulates the airflow through the mask 150 based on measured patient physiological parameters or some other criteria.

The CPAP mask 150 is typically worn at night and is intended to remain on while the patient sleeps. Because the patient is asleep during use, the patient is generally unable to manually or voluntarily act to keep the mask 150 in place. In an embodiment, the CPAP mask 150 is provided with one or more attachment structures 10 to generate electrostatic forces to hold the mask 150 in place on the patient. As discussed in other contexts, the attachment structures 10 may be powered and controlled by a power source and circuitry provided on the mask 150 itself or by external power and control circuitry provided as part of the ventilator and/or monitor and connected to the mask 150 by a conductive element, e.g., a wire. Likewise the attachment structures 10 may be made separate from the mask 150 and mechanically or chemically attached to the mask 150 or may be formed as an integral part of the mask 150.

The mask 150 may be made of a deformable or pliable material, such as a synthetic resin that, in conjunction with deformable attachment structures 10 may conform to the shape of the patient's face when held in place by electroadhesion, thus providing a tight fit for the mask 150. In an embodiment, the mask 150 may be held in place by electroadhesion alone, as depicted in the mask 150 of FIG. 10. However, as depicted in FIG. 11, the mask 150 may also be provided with lugs 154 that may be used for securing straps to the mask 150 that may also be used to secure the mask 150 to the patient.

In an embodiment, the mask 150 may include an input structure 44, such as a button or knob 152, that may be used by the patient to turn the electroadhesion on or off, allowing placement or removal of the mask 150 when appropriate. In addition, the button or knob 152 may allow adjustment of the amount of pressure applied by the mask 150 due to electroadhesion, thereby allowing the patient to customize the perceived pressure based on comfort and preference.

Further, in an embodiment, the mask 150 may include one or more pressure sensors 120 that provide a signal indicative of the pressure applied by the mask 150 on the patient. Such pressure data may be used by control circuitry 34 (FIG. 2) provided on the mask 150 or on a ventilator or monitor in communication with the mask 150 to vary the strength of the electrostatic forces used to hold the mask 150 in place or to maintain the pressure at a specified level or within a specified range. For example, the pressure sensors 120 may be used to provide a signal that may be used to determine if the mask 150 is slipping or becoming loose. Such a signal may then prompt control circuitry 34 to increase the strength of the electrostatic forces holding the mask 150 in place without disturbing the sleeping patient.

Figures 12, 13:
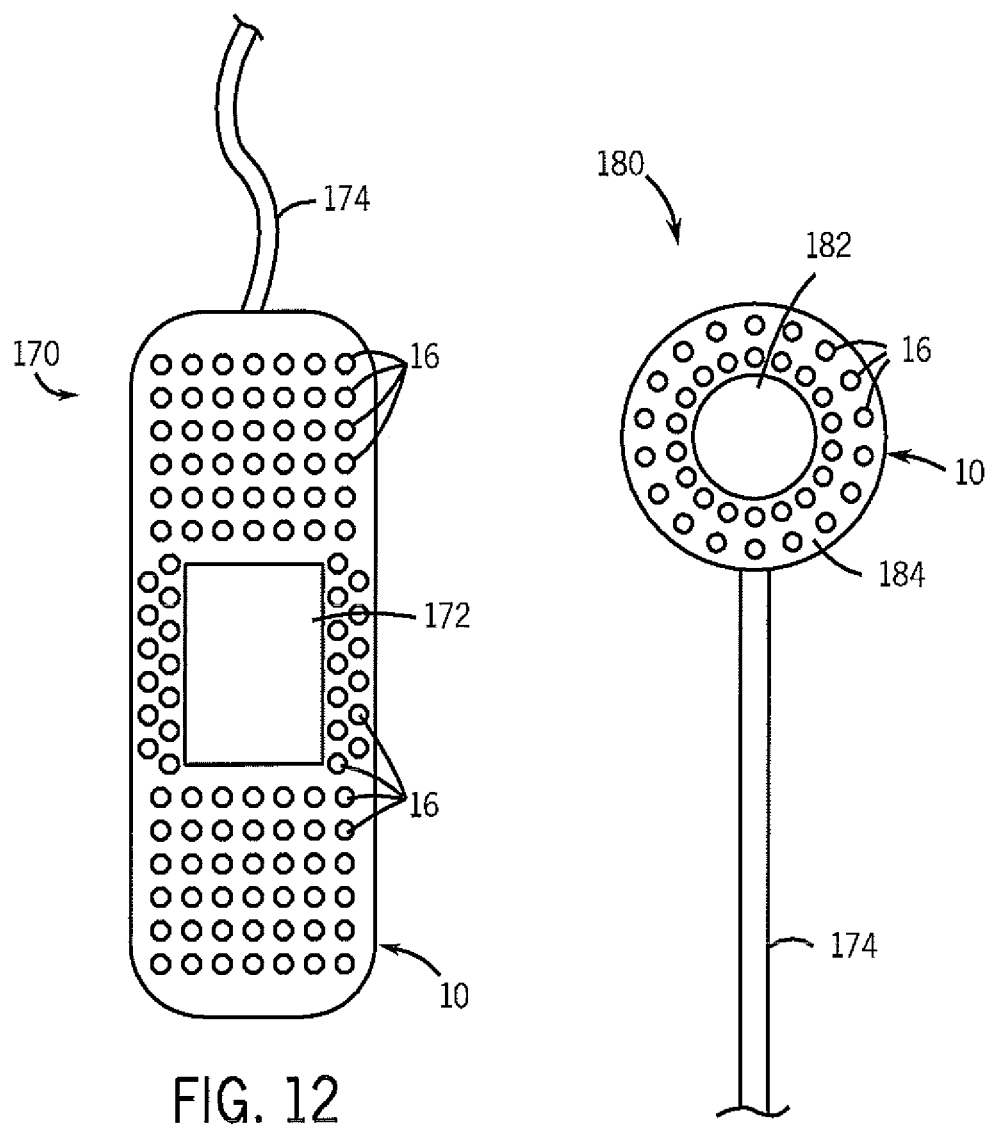
FIG. 12 depicts a bandage in accordance with an embodiment.
FIG. 13 depicts an electrode in accordance with an embodiment.

While the preceding describes the use of electroadhesion in securing a CPAP mask 150 to a patient, other respiratory devices and masks, including respiratory cannula, may be attached in a similar manner. Likewise, as discussed herein, other types of medical devices may also be secured in place using electroadhesion. For example, a bandage 170 (FIG. 12) may be formed integrally with the features of an attachment structure 10, e.g., insulating material 14 and electrodes 16, and may be secured to a patient by electroadhesion. Such a bandage 170 may include a gauze area 172 or other area suitable for contact with a wound and which may be applied with pressure to the patient via the electrostatic forces generated by the electrodes 16 on the bandage 170. In an embodiment, the bandage 170 may be connected to external power and/or operating circuitry via a cable 174. However, the bandage 170 may also be configured to include one or more of a power source or operating circuitry on the bandage itself, thus needing no cable 174 or external connection to remain in place by electroadhesion.

In another medical context, an attachment structure 10 as discussed herein may be provided as part of or attached to a monitor electrode 180 (FIG. 13) suitable for use in various applications, such as ECG or EEG. In an embodiment the monitoring electrode 180 may include a primary contact surface 182, by which the monitoring function performed by the monitoring electrode 180 are achieved, and a surrounding attachment ring 184 by which the monitoring electrode 180 is attached to the skin or tissue of the patient. In an embodiment, the attachment ring 184 may be formed integrally with the features of an attachment structure 10, e.g., insulating material 14 and electrodes 16, and may be secured to a patient by electroadhesion, in addition to or instead of chemical adhesives. Attachment structures 10 may also be separately formed and attached to the attachment ring 184 in other embodiments. The electrodes 16 used to provide electroadhesion may be connected to external power and/or operating circuitry via a cable 174, though some or all of these features may instead be supplied on the monitoring electrode 180.

In another embodiment electroadhesion may be used for devices attached to a patient for noninvasive drug delivery via absorption through the skin, such as a transdermal patch, and/or other drug deliver system.

While the invention may be susceptible to various modifications and alternative forms, specific embodiments have been shown by way of example in the drawings and have been described in detail herein. However, it should be understood that the invention is not intended to be limited to the particular forms disclosed. Indeed, while the preceding describes various example of medical contexts in which electroadhesion may be employed to apply and or hold a medical device or treatment to the skin, mucosal, or other tissues of a patient, such examples are merely intended to be illustrative and not exhaustive or limiting in any form. The invention is to cover all modifications, equivalents, and alternatives falling within the spirit and scope of the invention as defined by the following appended claims.

What is claimed is:

1. A structure for attachment to a patient, comprising:
   a pulse oximetry sensor; and
   an attachment structure formed integrally with the pulse oximetry sensor or physically coupled to the pulse oximetry sensor, the attachment structure comprising:
   a plurality of electrodes configured to generate differential voltages at adjacent electrodes, wherein the plurality of electrodes is constantly generating the differential voltages to attach the pulse oximetry sensor to the patient;
   a power supply configured to supply a voltage that may be used or conditioned to generate the differential voltage at the adjacent electrodes; and
   an insulative material between the respective electrodes of the plurality of electrodes.

2. The structure of claim 1, comprising control circuitry configured to determine one or more of the magnitude and timing of the differential voltages applied at the adjacent electrodes.

3. The structure of claim 1, comprising power conditioning configured to convert AC power to DC power, perform voltage smoothing, recover stored electrostatic energy, perform a voltage step-up of the differential voltages applied at the adjacent electrodes, or a combination thereof.

4. The structure of claim 1, comprising an input structure configured to adjust the differential voltages applied at the adjacent electrodes or of turning the differential voltages on and off.

5. The structure of claim 1, comprising a cable configured to attach the structure to one or more of a monitor or a therapeutic or treatment device.

6. The structure of claim 1, wherein one or both of the pulse oximetry sensor and the attachment structure conform to the patient when attached to the patient.

7. A method, comprising:
positioning a pulse oximetry sensor on a tissue of a patient;
applying differential voltages to adjacent electrodes of an attachment structure of the pulse oximetry sensor such that the differential voltages generate an electrostatic attraction with the tissue;
securing the pulse oximetry sensor to the tissue using the electrostatic attraction, wherein the differential voltages are constantly applied to maintain the electrostatic attraction with the tissue.

8. The method of claim 7, comprising adjusting the degree of electrostatic attraction using one or more input structures on the pulse oximetry sensor or in communication with the pulse oximetry sensor.

9. The method of claim 7, wherein the tissue comprises skin tissue or mucosal tissue.

10. The method of claim 7, wherein the pulse oximetry sensor, when secured, provides a clamping pressure of between about 0.5 N/cm$^2$ to about 1.5 N/cm$^2$ (about 0.8 lbs/in$^2$ to about 2.3 lbs/in$^2$).

11. The method of claim 7, wherein the differential voltages are between about 500 V to about 10 kV.

12. The method of claim 7, wherein the differential voltages are between about 2 kV to about 5 kV.

13. The method of claim 7, comprising alternating the differential voltages applied to adjacent electrodes.

14. A pulse oximetry sensor, comprising:
a sensor body;
an emitter disposed on the sensor body;
a detector disposed on the sensor body and configured to detect light emitted by the emitter; and
an attachment structure formed integrally with the sensor body or attached to the sensor body, the attachment structure comprising:
a plurality of electrodes wherein the plurality of electrodes is configured to constantly generate differential voltages to secure the sensor body to the patient;
a power supply configured to supply a voltage that may be used or conditioned to generate the differential voltage at the plurality of electrodes; and
an insulating material disposed between each of the respective electrodes of the plurality of electrodes.

15. The pulse oximetry sensor of claim 14, wherein the plurality of electrodes is configured to generate differential voltages at adjacent electrodes.

16. The pulse oximetry sensor of claim 14, wherein the sensor body comprises a bandage-style sensor body or a clip-style sensor body.

17. The pulse oximetry sensor of claim 14, comprising one or more of, control circuitry, power conditioning circuitry, or an input structure that affect a voltage applied to the plurality of electrodes.

* * * * *